(12) United States Patent
Portnoy

(10) Patent No.: US 10,940,262 B2
(45) Date of Patent: *Mar. 9, 2021

(54) PROTECTIVE MEDICAL DEVICE FACEPLATE

(71) Applicant: CERNER INNOVATION, INC., Kansas City, KS (US)

(72) Inventor: Alan Mark Portnoy, Exton, PA (US)

(73) Assignee: Cerner Innovation, Inc., Kansas City, KS (US)

( * ) Notice: Subject to any disclaimer, the term of this patent is extended or adjusted under 35 U.S.C. 154(b) by 184 days.

This patent is subject to a terminal disclaimer.

(21) Appl. No.: 15/703,526

(22) Filed: Sep. 13, 2017

(65) Prior Publication Data

US 2018/0001017 A1    Jan. 4, 2018

Related U.S. Application Data

(63) Continuation of application No. 15/394,322, filed on Dec. 29, 2016, now Pat. No. 9,789,246, which is a continuation-in-part of application No. 14/819,057, filed on Aug. 5, 2015, now Pat. No. 9,655,687.

(51) Int. Cl.
| | |
|---|---|
| *G06F 17/00* | (2019.01) |
| *A61M 5/142* | (2006.01) |
| *G06K 7/10* | (2006.01) |
| *A61B 90/96* | (2016.01) |
| *A61B 90/98* | (2016.01) |
| *G16H 10/60* | (2018.01) |
| *G16H 40/20* | (2018.01) |
| *A61M 5/14* | (2006.01) |

(52) U.S. Cl.
CPC ............ *A61M 5/142* (2013.01); *A61B 90/96* (2016.02); *A61B 90/98* (2016.02); *A61M 5/1415* (2013.01); *G06K 7/10297* (2013.01); *G16H 10/60* (2018.01); *G16H 40/20* (2018.01); *A61M 5/14* (2013.01); *A61M 2005/14208* (2013.01); *A61M 2205/3584* (2013.01); *A61M 2205/6054* (2013.01); *A61M 2205/6072* (2013.01)

(58) Field of Classification Search
CPC .......... G06F 17/00; G06F 19/00; G06K 7/10; A61M 5/142; A61M 5/14; A61B 90/96; A61B 90/98
USPC ........................... 235/375, 380, 454, 462.13
See application file for complete search history.

(56) References Cited

U.S. PATENT DOCUMENTS

| | | | |
|---|---|---|---|
| 5,389,711 A | 2/1995 | Westbrook et al. | |
| 5,389,771 A | 2/1995 | Amendolia | |
| 5,566,222 A | 10/1996 | Widemann et al. | |
| 6,747,578 B1 * | 6/2004 | Lam ..................... | G06F 1/1626 341/22 |

(Continued)

*Primary Examiner* — Karl D Frech
(74) *Attorney, Agent, or Firm* — Shook, Hardy & Bacon L.L.P.

(57) ABSTRACT

Devices are provided that include a faceplate for a medical device. In embodiments, an identifier chip adapted to be affixed to an exterior portion of a faceplate provides a unique identifier for the faceplate. Accordingly, the identifier chip enables tracking and monitoring of an associated medical device. And, in embodiments, the faceplate includes a visual communication alert indicator to enable the faceplate to provide visual cues a user. As such, the status of the medical device and the faceplate can be easily communicated to the user. Methods to use the faceplate are also provided.

19 Claims, 11 Drawing Sheets

(56) References Cited

U.S. PATENT DOCUMENTS

| | | |
|---|---|---|
| 6,956,572 B2 | 10/2005 | Zaleski |
| 7,278,589 B2 | 10/2007 | Wongosari et al. |
| 7,300,418 B2 | 11/2007 | Zaleski |
| 7,962,544 B2 | 6/2011 | Torok et al. |
| 8,291,337 B2 | 10/2012 | Gannin et al. |
| 8,990,722 B2 | 3/2015 | Gannon et al. |
| 9,218,455 B2 | 12/2015 | Neff |
| 9,501,619 B2 | 11/2016 | Portnoy et al. |
| 9,789,246 B2 * | 10/2017 | Portnoy ................ A61M 5/142 |
| 2007/0129983 A1 | 6/2007 | Scherpbier et al. |
| 2008/0120559 A1 * | 5/2008 | Yee ....................... G06F 1/1656 |
| | | 715/764 |

\* cited by examiner

PROTECTIVE MEDICAL DEVICE FACEPLATE

CROSS-REFERENCE TO RELATED APPLICATIONS

This application is a continuation of U.S. patent application Ser. No. 15/394,322, entitled "Protective Medical Device Faceplate," filed Dec. 29, 2016, which is a continuation-in-part of U.S. patent application Ser. No. 14/819,057, entitled "Protective Window for Medical Device Faceplates," filed Aug. 5, 2015, which is incorporated here by reference in its entirety.

BACKGROUND

Smart IV pumps are generally used to track and verify the infusion of prescribed medications within a hospital or clinical setting. Generally, a smart IV pump verifies the drugs it is dispensing with the medical record of a patient with whom the pump is associated and relies on an internally-stored medical formulary to determine a range of possible doses consistent with the orders stored in the medical record. However, to ensure that Smart IV pumps operate with the most recent formularies, the pumps rely on updates installed over a wireless network or manually installed by hospital personnel. Installing updates is often problematic. Hospital personnel can attempt to track down each and every pump to manually install an update. Alternatively, a hospital may attempt to use its internal wireless network to push an update to each smart pump. When an update is pushed through a wireless network, each individual pump can only install the update if the pump is powered on and not currently pumping. This requires that all pumps be left constantly powered on and plugged in to an uninterrupted power supply or the rechargeable battery to be charged, and the network must constantly push an update to all of the pumps until the last pump has installed the update. These problems have limited some hospitals to update Smart IV pump formularies only once or twice a year.

SUMMARY

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

Embodiments of the present invention relate to a device having a wireless computer integrated into a faceplate. In embodiments, the device includes a machine-readable identifier adapted to be removably affixed to an exterior surface of the faceplate. The machine-readable identifier encodes medical device-identifying information to enable tracking the medical device corresponding to the housing, in some embodiments. In embodiments, affixing the identifier activates the integrated wireless computer and automatically associates the faceplate with the machine-readable identifier. In embodiments, the machine-readable identifier is a modular chip configured to activate the faceplate module. In further embodiments, the modular chip comprises a metal exterior portion with an etched barcode that is resistant to staining and scratching.

In other embodiments, the device further includes a faceplate having an interior surface, an exterior surface, and a first opening for housing a window. The faceplate may be configured to be affixed to the housing of the medical device, in embodiments. In embodiments, when the faceplate is affixed to the housing, the window overlays at least a portion of the machine-readable identifier such that the at least a portion of the machine-readable identifier is visible therethrough from the exterior surface of the faceplate.

Embodiments of the present invention relate to a device having a wireless computer integrated with a faceplate having a protective window integrated with the faceplate. In embodiments, the device includes a communication port adapted to be removably affixed to an interior surface of a housing of a medical device, wherein the communication port communicates with the medical device and enables the faceplate device to install medical device upgrades. The device includes, in embodiments, a faceplate having an interior surface, an exterior surface, and an integrated wireless computer (such as a faceplate module), the faceplate configured to be removably affixed to the housing of a medical device.

Embodiments of the present invention relate to a device having a visual signifier to aid in identifying the status of an update. In embodiments, the device includes a visual communication alert indicator adapted to be affixed to an interior surface of a faceplate for a medical device. The indicator communicates the status of the faceplate and the medical device, in some embodiments. Additionally or alternatively, the faceplate includes an identifier chip configured to allow tracking of the faceplate and the medical device by a user.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different components, combinations of components, steps, or combinations of steps similar to those described in this document, in conjunction with other present or future technologies.

Embodiments of the present invention are directed toward a wireless computer implemented with or integrated into a faceplate of a medical device, such as an infusion pump, for example. The computer enables an update to the medical device to be stored, for example, until a time at which the medical device is able to receive the update. In this way, the computer prevents unnecessary bandwidth consumption associated with pushing a medical device update over a wireless network and/or the drain of hospital personnel tracking down each and every pump to ensure an update is installed.

Figure 1:
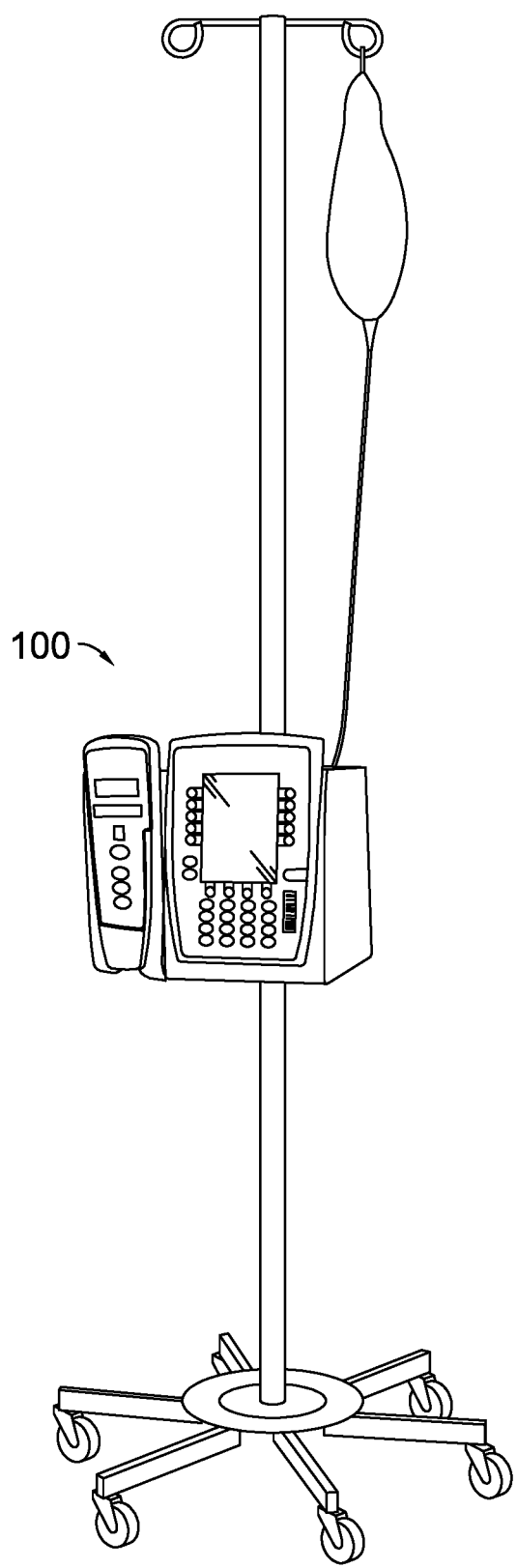
FIG. 1 is an exemplary medical device including a faceplate, in accordance with an embodiment of the invention.

Referring initially to FIG. 1, an exemplary medical device having a faceplate, with which embodiments of the present invention may be implemented, is illustrated and designated generally as reference numeral 100. It will be understood and appreciated by those of ordinary skill in the art that the illustrated medical device 100 is merely an example of one suitable medical device and is not intended to suggest any limitation as to the scope of use or functionality of the invention. Neither should the medical device 100 be interpreted as having any dependency or requirement relating to any single component or combination of components illustrated therein.

Embodiments of the present invention may be operational with numerous other general purpose or special purpose medical devices. The medical device 100 may be any device, stationary or otherwise, that may be used to treat a patient in a clinical setting, such as a hospital, a health care clinic, a doctor's office, a blood drive, etc. For exemplary purposes only and not limitation, medical devices may include fetal heart rate monitors, blood pressure monitors, uterine pressure and contraction activity monitors, blood oxygen saturation monitors, maternal heart rate monitors, other monitors, ventilators, pumps (e.g., balloon pumps), a patient's bed, sequential compression devices, electronic security devices, and the like. In further embodiments, the present invention may be implemented for use with medical devices having highly sensitive patient monitoring capabilities and/or highly accurate treatment-delivery mechanisms. Commonly referred to as "smart" medical devices, such medical devices typically interface with computing hardware and software that may be employed to control, adjust, and tailor performance of one or more functions of said medical devices and any auxiliary components or devices coupled thereto. Accordingly, smart medical devices may generally be connected to a wireless network so as to provide real-time, continuous, and intelligent care delivery, unlike more passive medical devices of the past. Examples of smart medical devices that may be suitable for use with the present invention include, by way of example only, pumps (e.g., infusion), end title carbon dioxide (EtCO2) modules, and other sophisticated and technology-driven devices.

In a clinical setting, the management and treatment of a single patient may command the use of a plurality of medical devices for monitoring physiological responses, delivering therapeutic agents (e.g., pharmaceuticals, fluids), and the like. In order to deliver superior health care to patients, a large number and variety of medical devices may be utilized and employed. In addition to manual maintenance (e.g., on moving parts) performed on medical devices, smart medical devices in particular may utilize software and/or hardware-based maintenance, such as the download of a firmware update, for example.

Figure 2:
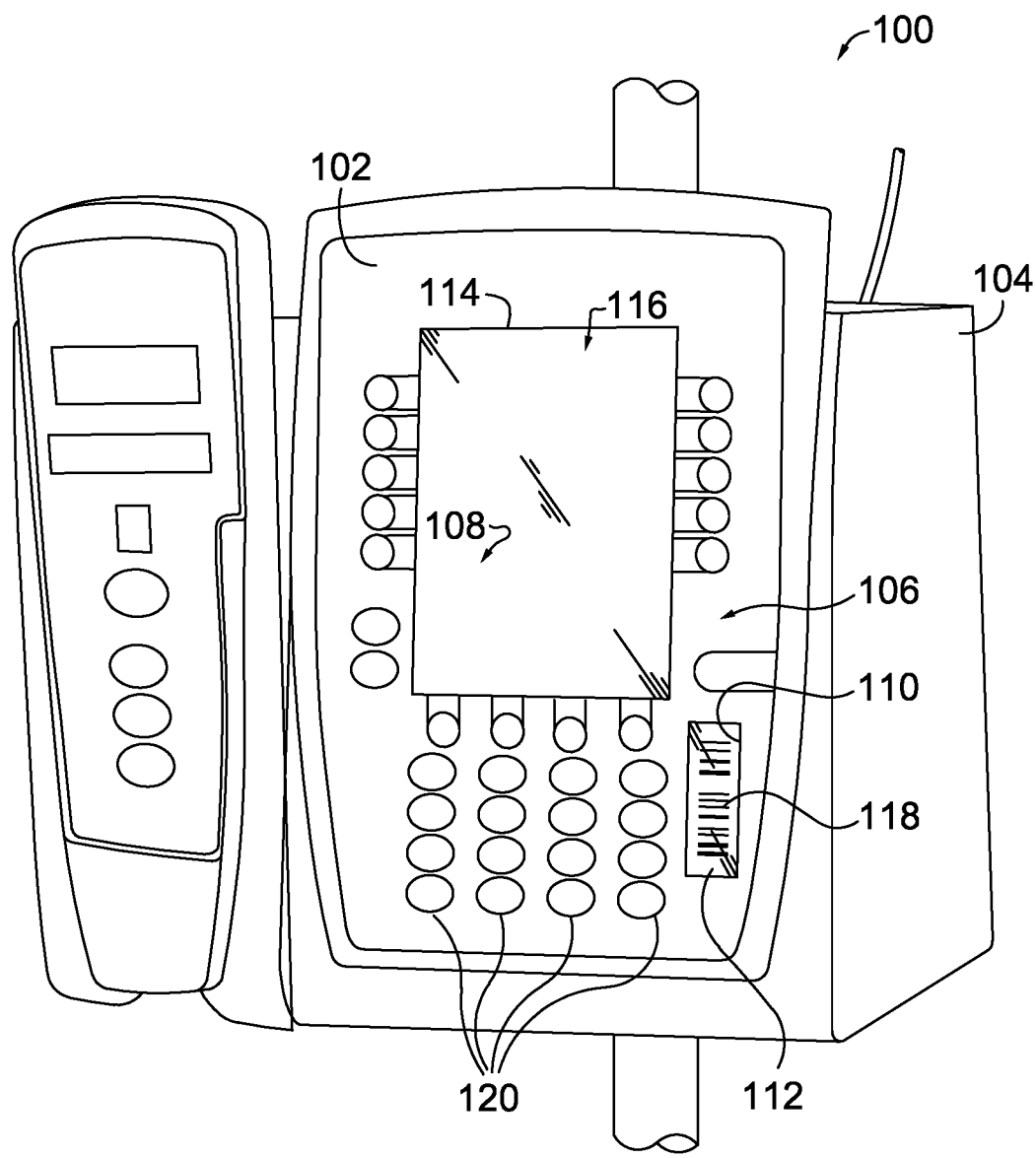
FIG. 2 is a right perspective detail view of the exemplary medical device including a faceplate shown in FIG. 1, in accordance with an embodiment of the invention.

Turning to FIG. 2, it depicts a right perspective view of the exemplary medical device 100 including the faceplate 102 shown in FIG. 1, in accordance with an embodiment of the present invention. The faceplate 102 is a component that generally provides a user interface (e.g., buttons, knobs) for interacting with the medical device 100. Accordingly, the faceplate 102 is configured to be affixed to the housing 104 of the medical device 100. In some embodiments, the faceplate 102 is adapted to be removably affixed to the medical device 100 (e.g., housing 104) such that the faceplate 102 may stay securely in place during use and transport of the medical device 100, but such that the faceplate 102 may also be removed should the faceplate 102 need to be replaced and/or repaired. In general, the faceplate is removably affixed, meaning that the faceplate is configured to be affixed to the medical device 100 and configured to be removed from the medical device 100 without damaging the faceplate, for example. The faceplate 102 includes an interior surface (not shown) and an exterior surface 106. The exterior surface 106 may be outward and/or upward facing with respect to the internal components of a medical device 100, and as such, a clinician may easily access and view the exterior surface 106 of the faceplate 102 when a clinician is in a standing position at the bedside of a patient, for example. The faceplate 102 serves to provide information to a clinician and enable the clinician to control, program, and/or otherwise operate the medical device using buttons, knobs, dials, and the like. The faceplate 102 may protect a graphical user interface (GUI) 108 such as a touchscreen display. A GUI may include a monitor, computer screen, project device, or other hardware device for displaying output capable of displaying graphical user interfaces. The faceplate 102 provides a clean, aesthetically pleasing appearance while covering at least a portion of the medical device 100, including internal components and/or a GUI 108, in some embodiments. The faceplate 102 may further protect the medical device and components therein from spills, splashes, cleaning solvents, scratches, and impacts.

In embodiments, the faceplate 102 includes an opening 110 for housing a window 112. The opening 110 is adapted to receive at least a portion of a window 112, in embodiments. The opening 110 may further be adapted to securely retain at least a portion of a window 112 inserted or positioned therein. Generally, the opening 110 may be similar or the same in size and shape as a window 112 adapted for said opening 110. In further embodiments, the position and dimensions of a first opening 110 correspond to the position and dimensions of a first window (e.g., 112) and the machine-readable identifier 118, while the position and dimensions of a second opening (e.g., opening 114) correspond to the position and dimensions of a second window (e.g., window 116) further corresponding to the GUI 108 of a medical device 100.

In embodiments, window 112 is adapted to be secured to the faceplate 102 so as to span opening 110 completely or at least partially. In some embodiments, window 112 is adapted to be integrated into opening 110. The window 112 is at least semi-transparent, in embodiments. In some embodiments, the window 112 comprises one or more materials that are semi-transparent or transparent. The window 112 provides visibility via the opening 110 of the faceplate 102 from the exterior surface 106 of the faceplate 102. As such, the window 112 may be positioned so that a machine-readable identifier 118 is visible when the faceplate 102, as affixed to the exemplary medical device 100, is viewed from the exterior surface 106 of the faceplate 102.

In some embodiments, the medical device 100 may need refurbishment or replacement of parts, such as the faceplate 102 that fits onto the housing 104 of the medical device 100. The faceplate 102 may include a plurality of objects 120 for user interaction. In embodiments, the faceplate 102 may include one or more of the following objects for controlling, programming, and adjusting configurations and functions of the medical device: a GUI (e.g., 108), I/O components, physical buttons, virtual buttons, switches, dials, knobs, a keyboard, and the like, for example. The plurality of objects 120 may be manipulated by a user, such as a clinician, in order to use the medical device 100 to provide health care services to a patient. Over time, one or more of the plurality of objects 120 may wear out from use, such that at least one of the objects 120 may be unresponsive when depressed, may necessitate the use of extra force to elicit the desired response (e.g., selection of an option indicated on the GUI 108, increasing an amount to be dispensed by a medical device, setting a flow rate), or may necessitate the use several depressions to register a single depression that elicits a response. This makes interaction with the medical device 100 an inconvenience and an annoyance for clinicians. At such a time, any worn-out, malfunctioning, and/or poorly operating objects of the faceplate 102 may be replaced to restore fully functioning interactive objects to the medical device 100.

A machine-readable identifier 118, such as a barcode for example, may be visible at the faceplate 102, in some embodiments. Exemplary machine-readable identifiers include a one-dimensional barcode (e.g., a Codabar), a two-dimensional barcode (e.g., a quick response (QR) code), and the like. The machine-readable identifier 118 may encode medical device-specific information, such as an identifier that is unique to a single medical device such that the medical device may be differentiated from other same or similar medical devices.

The machine-readable identifier 118 may be used to enable tracking of a particular medical device, including the use, function, repair, and storage of said medical device, in a clinical setting, for example. The machine-readable identifier 118 may be utilized in any number of useful ways. For instance, using a machine, such as a barcode scanner, for example, the machine-readable identifier 118 may be scanned and information encoded therein or linked to therein may be "read" by a barcode scanner for example, or processed to locate information corresponding to the machine-readable identifier 118.

Exemplary machines for reading the machine-readable identifier 118 may include a barcode scanner, a camera, a sensor, and other devices having I/O components and software for processing the information stored in, associated with, or linked to the machine-readable identifier 118. The medical device 100 and faceplate 102 corresponding to the machine-readable identifier 118 may be associated with other information accessed, selected, scanned, or otherwise read immediately prior to or immediately after the machine-readable identifier 118 has been read, in some embodiments.

For example, a patient-identifying wristlet may be scanned, followed by a scan of an intravenous (IV) fluid to be administered to the patient, and further followed by a scan of the machine-readable identifier 118 of the medical device 100, which is to be used to administer the scanned IV fluid to the patient having the scanned wristlet. In such an embodiment, detailed and identifying information for each of the medical device 100, the IV fluid, and the patient may be electronically linked in an electronic medical record (EMR), for example. The machine-readable identifier 118 may, in some embodiments, enable the particular medical device 100 corresponding to the scanned machine-readable identifier 118 to become associated with an identified patient, an EMR corresponding to the particular identified patient, and/or with a particular instance of administration of a therapeutic agent, for example.

As utilized herein, the acronym "EMR" is not meant to be limiting, and may broadly refer to any or all aspects of the patient's medical record rendered in a digital format. Generally, the EMR is supported by systems configured to coordinate the storage and retrieval of individual records with the aid of computing devices. As such, a variety of types of health care related information may be stored and accessed in this way. By way of example, the EMR may store one or more of the following types of information: patient demographic; medical history (e.g., examination and progress reports of health and illnesses); medicine and allergy lists/immunization status; laboratory test results, radiology images (e.g., X-rays, CTs, MRIs, etc.); evidence-based recommendations for specific medical conditions; a record of appointments and physician's notes; billing records; and data received from an associated medical device. Accordingly, systems that employ EMRs reduce medical errors, increase physician efficiency, and reduce costs, as well as promote standardization of health care.

In embodiments, upon reading the machine-readable identifier 118, the medical device 100 and faceplate 102 corresponding therewith may become associated with a maintenance order, for example, a work order to replace the faceplate 102, swap the faceplate 102, purchase a new faceplate, or other action regarding the medical device 100 and/or faceplate 102. In another embodiment, the machine-readable identifier 118 may be read to electronically record the status of a maintenance order, for example, to document a time, date, and/or location corresponding to when repair work is initiated, is in progress, is delayed for a part shipment, and/or has been completed. In yet another embodiment, upon reading a machine-readable identifier 118, the medical device 100 and faceplate 102 corresponding therewith may be counted as part of an inventory check, such as placement of the medical device 100 into storage (e.g., when the medical device 100 is not to be used) or removing the medical device 100 from storage (e.g., when the medical device 100 is planned to be used).

Due to the position of the machine-readable identifier 118 on the faceplate 102, said machine-readable identifier 118 may be lost due to faceplate 102 replacement, removed accidently by peeling, or otherwise obliterated by cleaning solvents and other wear and tear. To circumvent this, the machine-readable identifier 118 may be placed elsewhere on the medical device 100 in other embodiments. However, this makes locating the machine-readable identifier 118 difficult for a clinician, and further may make reading the machine-readable identifier 118 unwieldy, depending on the final placement of the machine-readable identifier 118 on a surface of the medical device 100.

As depicted in FIG. 2, a machine-readable identifier 118 is visible at the exterior surface 106 of the faceplate 102. The machine-readable identifier 118 may be adapted to be affixed to an interior surface of a housing 104 of a medical device 100. For example, the machine-readable identifier 118 may be included on an adhesive-backed label that may be affixed to an interior surface of the housing 104 of the medical device 100. As referred to herein, an interior surface of the medical device housing refers to a surface of the medical device 100 that may be, at least, partially covered or contacted by the faceplate 102 affixed thereon in embodiments. In some embodiments, the interior surface of the medical device housing 104 is a surface of the housing 104 that is adapted to contact and/or receive at least a portion of an interior surface (not shown in FIG. 2) of the faceplate 102 and/or attachment means thereon. Accordingly, the machine-readable identifier 118 may be positioned at or on the interior surface of the housing 104 such that the position and at least one dimension (e.g., size, width, shape) of the machine-readable identifier 118 may be similar to the position and at least one dimension of the window 112 that may be housed in the opening 110 of the faceplate 102. For example, the length of a machine-readable identifier 118 may be the same as or similar to the length of the opening 110 and/or the window 112. In another example, the length and width of the machine-readable identifier 118 may be the same as or similar to the length and width of the opening 110 and/or the window 112. In such exemplary embodiments, one or more dimensions and/or a position of the machine-readable identifier 118 may, at least, partially align with one or more dimensions and/or a position of the window 112 when the faceplate 102 is affixed to the housing 104. As such, when the faceplate 102 may be affixed to the housing 104, the machine-readable identifier 118 appears to be aligned with the window 112 such that a clinician has a clear line-of-sight of the machine-readable identifier 118 from the exterior surface 106 of the faceplate 102.

Figure 3:
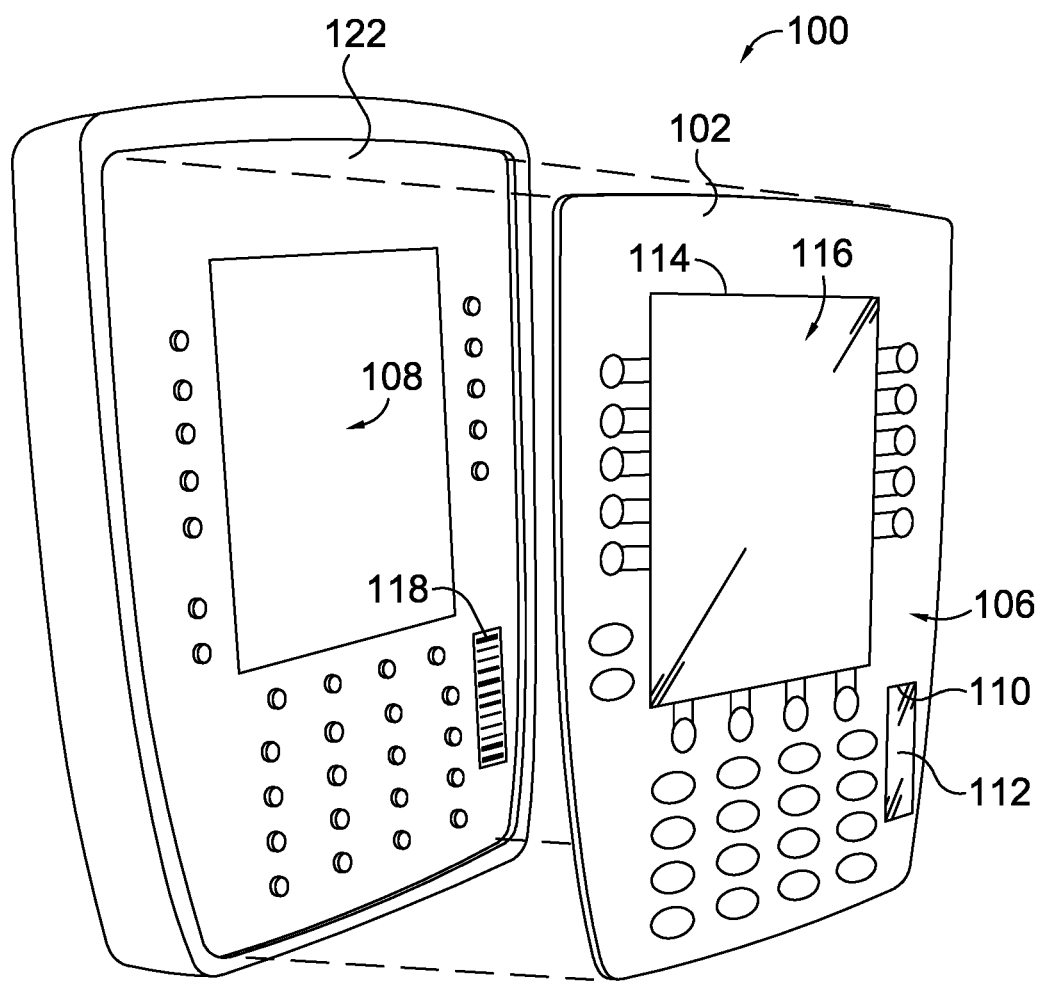
FIG. 3 is an exploded perspective view of the exemplary medical device including a faceplate shown in FIG. 1, in accordance with an embodiment of the invention.

Turning now to FIG. 3, it depicts an exploded view of the exemplary medical device 100 including a faceplate 102 shown in FIG. 1, in accordance with an embodiment of the present invention. As illustrated in FIG. 3, the position of the machine-readable identifier 118 and the position of the window 112 may at least partially align with one another. In further embodiments, at least one window (e.g., window 112) overlays at least a portion of the machine-readable identifier 118 so that the at least a portion of the machine-readable identifier 118 is visible at the exterior surface 106 of the faceplate 102. Additionally, the window 112 shown as positioned in opening 110 provides protection to the machine-readable identifier 118, such that the machine-readable identifier 118 may be enclosed between the interior surface of the faceplate 102 and the interior surface 122 of the housing 104 of the medical device 100. Similarly, a second window (e.g., window 116) shown positioned in second opening 114 provides protection to the GUI 108 of a medical device 100.

Although the faceplate 102 depicted in FIG. 3 appears to fit snugly into the housing 104 of the medical device 100, it will be understood by those in the art that other configurations are considered to be within the scope of the invention. For example, the faceplate 102 may fit onto the housing 104, rather than into the housing 104. In another example, the faceplate 102 may fit over the housing 104. Any number of variations for attaching the faceplate 102 to the housing 102 is considered to be within the scope of the invention.

Figure 4:
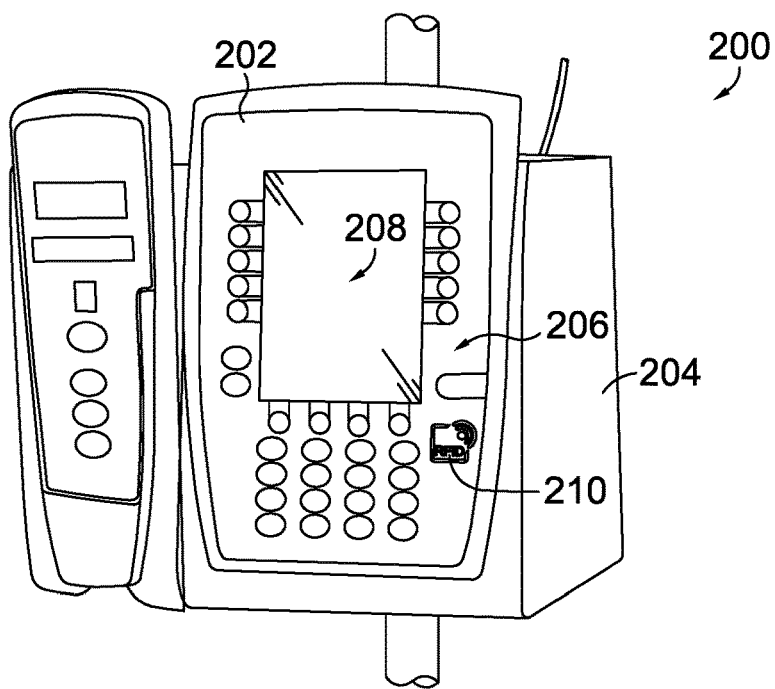
FIG. 4 is a plan view of an exterior surface of an exemplary faceplate for a medical device, in accordance with an embodiment of the invention.

Referring to FIG. 4, it illustrates a perspective view of faceplate 202 for an exemplary medical device 200. The faceplate 202 is coupled to a housing 204 of the medical device 200, as shown in the embodiment of FIG. 4. The faceplate 202 includes an exterior surface 206. The exterior surface 206, generally, is outward and/or upward facing with respect to internal components of the medical device 200, and as such, a clinician may easily access and view the exterior surface 206 of the faceplate 202 when a clinician is in a standing position at the bedside of a patient, for example. The faceplate 202 serves to provide information to a clinician and enable the clinician to control, program, and/or otherwise operate the medical device 200 using buttons, knobs, dials, and the like. The faceplate 202 may protect a GUI 208, such as a touchscreen display, for example.

The exterior surface 206 further includes a visual signifier 210. The visual signifier 210 is configured to visually communicate the location of an identifier affixed to an interior surface of the faceplate 202. In some embodiments, the identifier is an RFID-emitting device (e.g., a tag or a chip) that may be affixed to an interior surface of the faceplate 202. In another embodiment, the identifier is adapted for use in a real-time locating system (RTLS), wherein real-time as used herein may include latency inherent to computing systems. As used herein, visually communicate refers to the capability to communicate a message to a user, such as a clinician for example, visually. A visual signifier 210, as used herein, refers to text, a symbol, an icon, a graphic, or combination thereof that may be associated with a message or function. For example, an exclamation point centered within a triangular shape is a symbol that may be recognized by a user as communicating "caution."

In another example, a small circle having three concentric circle segments radiating upward the outward from the small circle and graduating in size may be recognized by a user as communicating Wi-Fi functionality. The visual signifier 210 may also include color to communicate a desired message or functionality. For example, a red-colored letter "X" may be recognized to communicate a cancellation function or a stop function. The size of the visual signifier 210 may be used to communicate information as well. For instance, the visual signifier 210 may have a size and dimensions that are the same as or similar to the size and dimensions (e.g., a "footprint") of an RFID device, such that the visual signifier 210 indicates an area where an RFID-reading device may be placed at or near the exterior surface 206 for reading the RFID device at or near the interior surface. In another embodiment, the visual signifier 210 may not similar in size and/or dimension (e.g., a "footprint") of a device (e.g., a tag) adapted for user in a real-time location system (RTLS), such that the visual signifier 210 indicates that said device is associated with the faceplate 202. In another example, a device (e.g., tag adapted for use in a RTLS) may be found without requiring a locating device to be placed at or near the exterior surface 206, for example.

In another example, the visual signifier 210 may incorporate a light, such as an LED for example, as part of the visual signifier 210 in order to draw a user's eye to the area of the visual signifier 210 as positioned on the exterior surface 206 of the faceplate 202. In embodiments, the position of the visual signifier 210 on or at the exterior surface 206 of the faceplate 202 corresponds to a location of the RFID device. As such, a clinician may position an RFID-reading device close to or near the visual signifier 210 in order to read an RFID device located therein. In some embodiments, a passive RFID device requires an RFID-reading device to be within a defined distance or proximity to the RFID device in order to trigger an emission of an RFID from the RFID device.

Figure 5:
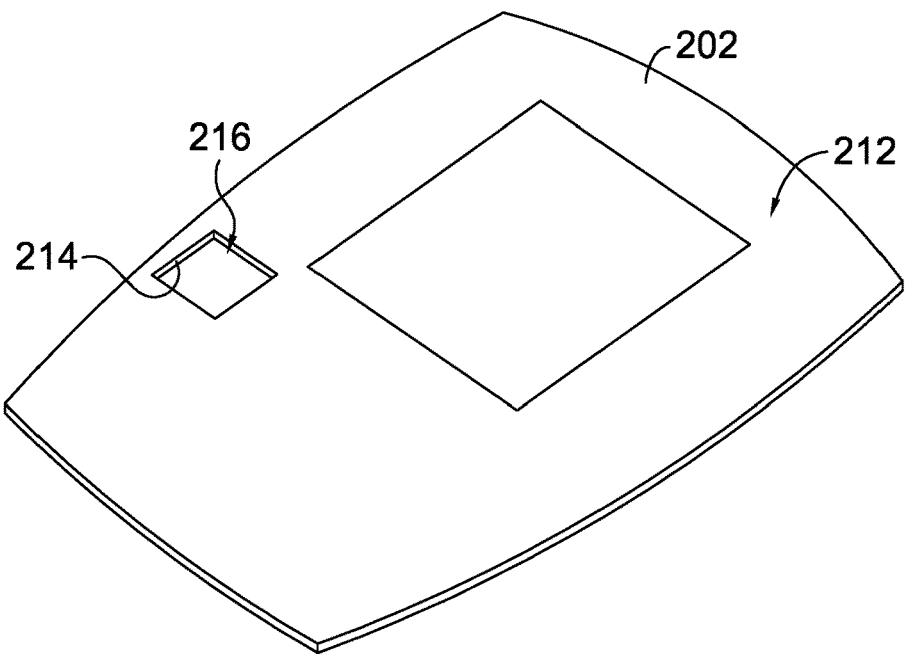
FIG. 5 is a plan view of an interior surface of the exemplary faceplate of FIG. 4, in accordance with an embodiment of the invention.

Referring to FIG. 5, it illustrates a perspective view of the exemplary faceplate 202 of FIG. 4, in accordance with an embodiment of the present invention. As illustrated, the faceplate 202 includes an interior surface 212. The interior surface 212 of the faceplate 202 includes at least one portion 214 adapted to receive a device for tracking, such as a "tag" or chip adapted for use with RFID systems or RTLS (not shown). The interior surface 212 of the faceplate 202 may include one or more edges 216 that form a perimeter of the at least one portion 214 of the interior surface 212. In some embodiments, the at least one portion 214 is recessed. As such, the device for tracking may be inserted into said recess created by the portion 214. The one or more edges 216 may aid in securing a device for tracking therein. In embodiments, the interior surface of the faceplate includes attachment means for receiving the device for tracking and retaining the device for tracking therein.

Figure 6:
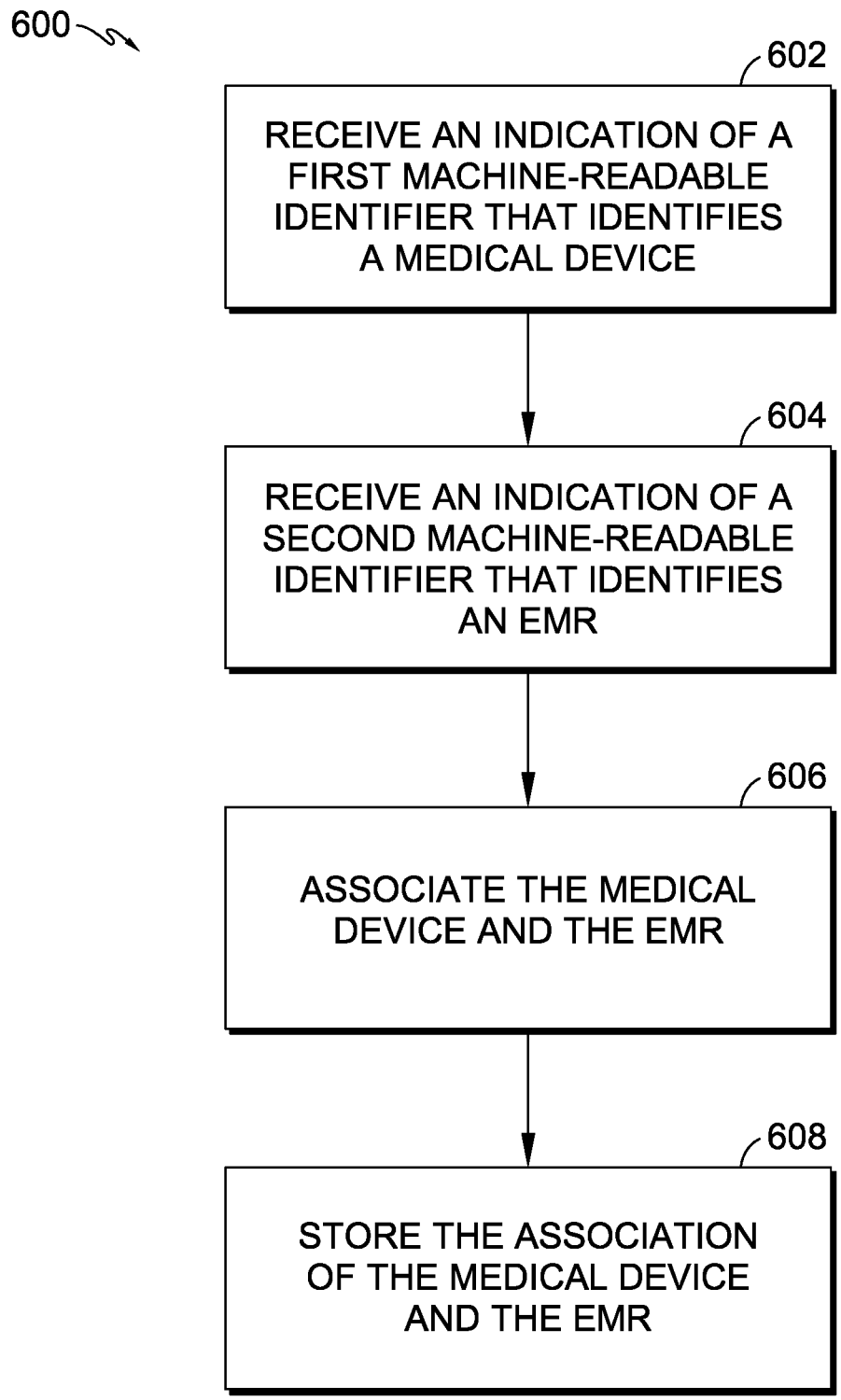
FIG. 6 is an illustrative flow diagram of an exemplary method for utilizing a machine-readable identifier, in accordance with an embodiment of the invention.

Turning to FIG. 6, it illustrates a flow chart of an exemplary method 600 for utilizing a machine-readable identifier, in accordance with an embodiment of the present invention. At block 602, the method 600 includes receiving an indication of a first machine-readable identifier. In some embodiments, the first machine-readable identifier may be affixed to an interior surface of a housing of a medical device. The first machine-readable identifier may be affixed to an interior surface of a faceplate, in other embodiments. Generally, the first machine-readable identifier is usable to identify and distinguish the medical device from other medical devices. In one embodiment, the first machine-readable identifier is a barcode visible through a window of a faceplate of a medical device. In some embodiments, the first machine-readable identifier that includes a barcode is read using a scanning device.

In another embodiment, the first machine-readable identifier is a RFID that is not visible at the exterior surface of a faceplate of a medical device. In some embodiments, the first machine-readable identifier that includes an RFID (e.g., a near field communication identifier tag) is read by a capable device. An RFID may be passive or active, such that a passive RFID is not coupled to a power source (e.g., passive RFID may be powered by an electromagnetic field generated by the RFID reader), whereas an active RFID is coupled to a power source (e.g., a battery). In further embodiments, the first machine-readable identifier includes one or more of a barcode and an RFID, such that a scanning device and or an RFID-reading device may be used to identify the medical device.

In another embodiment, the first machine-readable identifier is a tag adapted for use in an RTLS that is not visible at the exterior surface of a faceplate of a medical device. In some embodiments, the first machine-readable identifier that includes a tag adapted for use in an RTLS is read or located by a capable device. In further embodiments, the first machine-readable identifier includes one or more of a barcode and a tag adapted for use in an RTLS, such that a locating device and or reading device may be used to identify the medical device At block 604, the method 600 includes receiving an indication of a second machine-readable identifier that is not the same as the first machine-readable identifier, wherein the second machine-readable identifier is usable to identify an electronic medical record of a patient. Next, the medical device and the EMR of the patient are associated with one another, shown at block 606. The first machine-readable identifier corresponding to the medical device may be associated with and/or linked to the second machine-readable identifier corresponding to the patient. Then at block 608, the association of the medical device and the EMR is stored. The association of the medical device and the EMR may be stored in a local database, a centralized database, or both, for redundancy. Similarly, in embodiments, an association of a first machine-readable identifier corresponding to the medical device and a second machine-readable identifier corresponding to the EMR may be stored. It will be understood by those in the art that the method 600 may be practiced utilizing exemplary device 200, for example.

Figure 7:
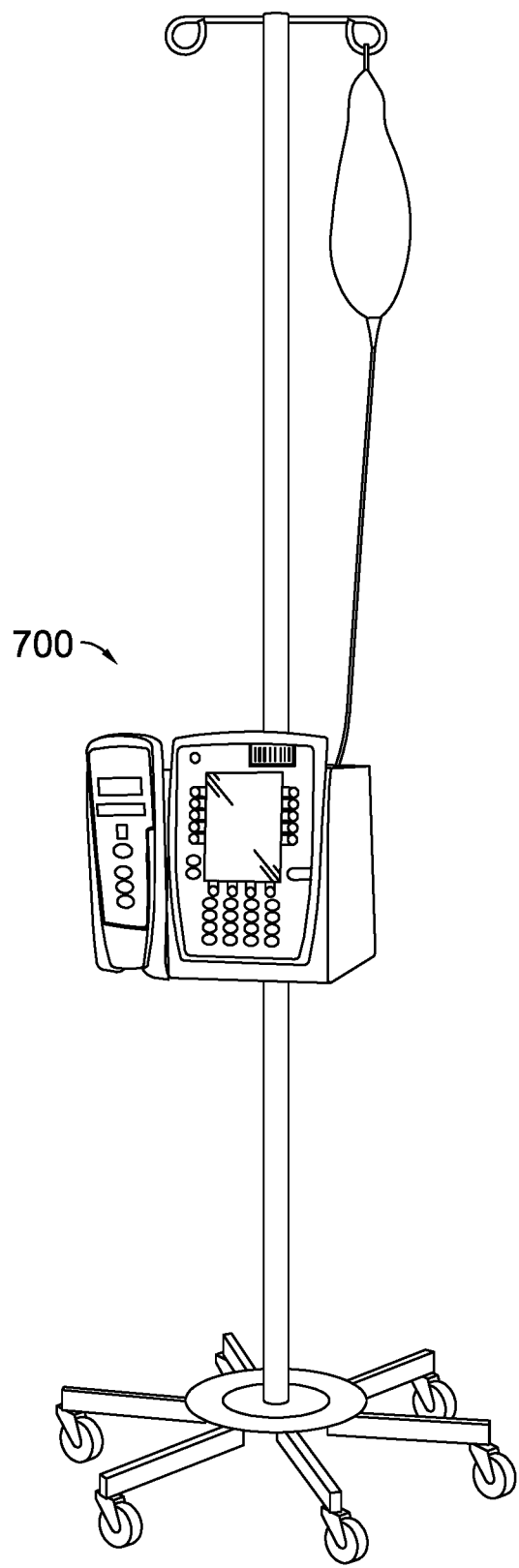
FIG. 7 is another exemplary medical device including a faceplate, in accordance with an embodiment of the invention.

Turning to FIG. 7, another exemplary medical device having a faceplate, with which embodiments of the present invention may be implemented, is illustrated and designated generally as reference numeral 700. It will be understood and appreciated by those of ordinary skill in the art that the illustrated medical device system 700 is merely an example of one suitable medical device and is not intended to suggest any limitation as to the scope of use or functionality of the invention. Neither should the medical device system 700 be interpreted as having any dependency or requirement relating to any single component or combination of components illustrated therein.

Figure 8:
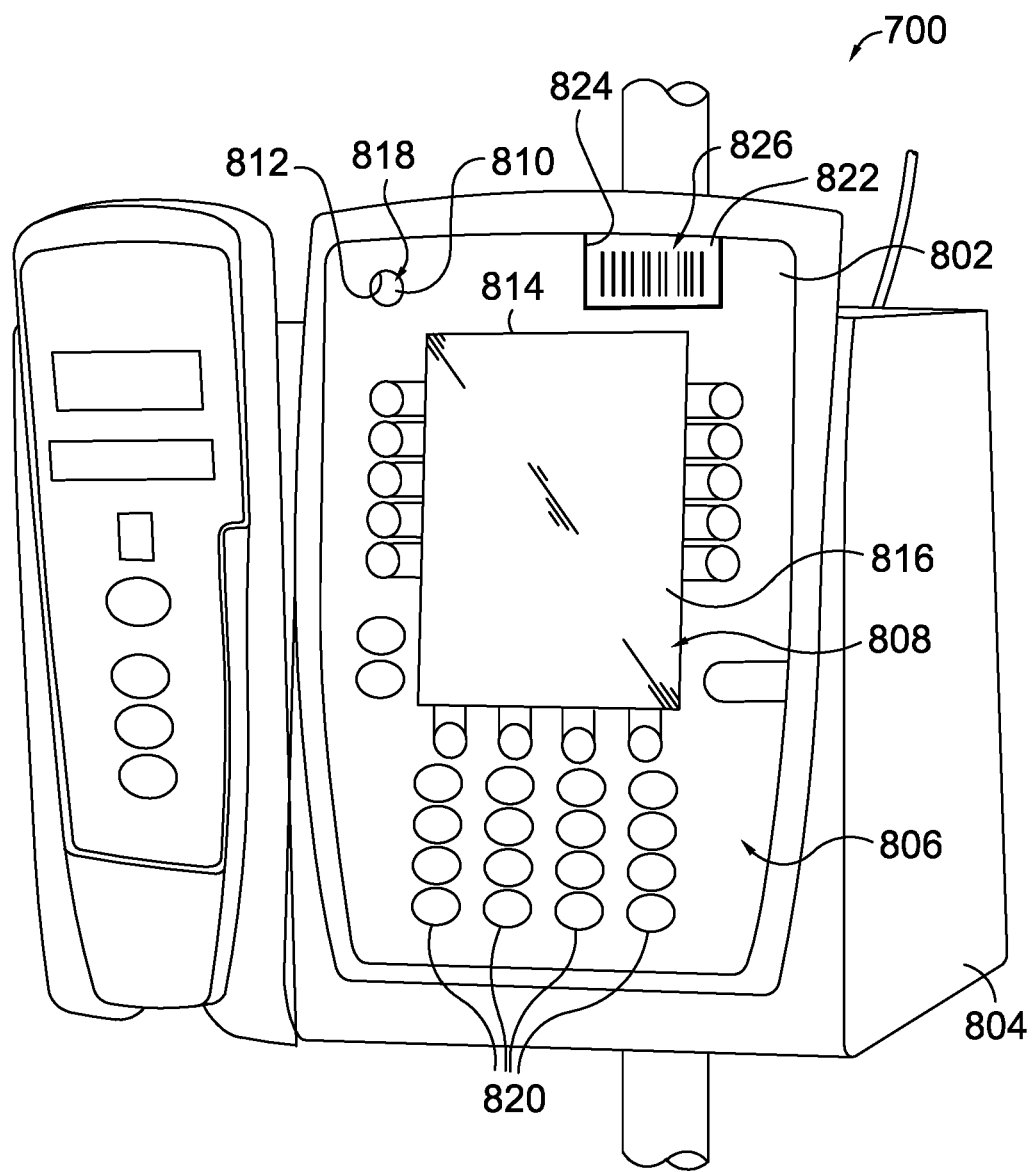
FIG. 8 is a right perspective detail view of the exemplary medical device including a faceplate shown in FIG. 7, in accordance with an embodiment of the invention.

FIG. 8 depicts a right perspective view of the exemplary medical device 700 including the faceplate 802 shown in FIG. 7, in accordance with an embodiment of the present invention. The faceplate 802 includes an integrated slot 824 which is adapted to receive and house at least a portion of an identifier chip 822, in embodiments. The integrated slot 824 may be further adapted to securely retain at least a portion of the identifier chip 822. For example, in embodiments not depicted, the integrated slot 824 may further comprise a retaining mechanism, such as a retaining clip, slide, lock, or any mechanism or mechanisms that may be configured to securely retain, at least temporarily, identifier chip 822. Generally, the integrated slot 824 may be similar or the same in size and shape as the identifier chip 822 adapted for said integrated slot. 824.

An identifier chip 822 may be visible at the faceplate 802, in some embodiments. In embodiments, the identifier chip 822 may contain a machine-readable identifier 826. Exemplary machine-readable identifiers include a one-dimensional barcode (e.g., a Codabar), a two-dimensional barcode (e.g., a quick response (QR) code, and the like. In embodiments, the machine-readable identifier 826 may be permanently etched in a metallic portion (not shown) of the identifier chip 822. Exemplary machines for reading the machine-readable identifier 826 may include a barcode scanner, a camera, a sensor, and other devices having I/O components and software for processing the information stored in, associated with, or linked to the machine-readable identifier 826.

The machine-readable identifier 826 may encode information that is unique to a single medical device such that the medical device may be differentiated from other same or similar medical devices. In some embodiments, the machine-readable identifier 826 may encode information unique to the identifier chip 822 itself, such that a medical device 804 may be associated with the identifier chip 822 and may be differentiated from other same or similar medical devices by its association therewith. The machine-readable identifier 826 may be used to enable tracking of activities relating to a particular medical device, including its use, function, repair, and storage, for example. For instance, using a machine such as a barcode scanner, the machine-readable identifier 826 may be scanned and information encoded therein or linked thereto may be read or processed to locate or display information corresponding to the machine-readable identifier 826 or the medical device 804 with which it is associated.

The medical device system 700, faceplate 802, and identifier chip 822 corresponding to the machine-readable identifier 826 may be associated with other information accessed, selected, scanned, or otherwise read immediately prior to or immediately after the machine-readable identifier 826 has been read, in some embodiments. The machine-readable identifier 826 may, in some embodiments, enable the particular medical device system 700 corresponding to the scanned machine-readable identifier 826 to become associated with an identified patient, an EMR corresponding to a particular identified patient, and/or with a particular instance of administration of a therapeutic drug agent. For example, a patient-identifying wristlet, an intravenous (IV) fluid to be administered to a patient, and the machine-readable identifier 826 for the medical device system 700 may each be scanned in sequence to create an EMR entry reflecting that the scanned IV fluid was administered to the patient having the scanned wristlet by use of the medical device system 700. Additionally in embodiments, an association between the particular medical device system 700 and an EMR corresponding to a particular identified patient may enable data contained in the EMR to be transferred to the particular medical device system 700. For example, the EMR may contain an order for the administration of a therapeutic drug agent. Once an association between a particular medical device system 700 and the EMR is established the order for the administration of the therapeutic drug agent may be automatically transferred to the particular medical device system 700.

As utilized herein, the acronym "EMR" is not meant to be limiting, and may broadly refer to any or all aspects of the patient's medical record rendered in a digital format. Generally, the EMR is supported by systems configured to coordinate the storage and retrieval of individual records with the aid of computing devices. As such, a variety of types of health care-related information may be stored and accessed in this way. By way of example, the EMR may store one or more of the following types of information: patient demographic; medical history (e.g., examination and progress reports of health and illnesses); medicine and allergy lists; immunization status; laboratory test results; radiology images (e.g., X-rays, CTs, MRIs, etc.); evidence-based recommendations for specific medical conditions; a record of appointments and physicians' notes; billing records; and data received from an associated medical device. Accordingly, systems that employ EMRs reduce medical errors, increase physician efficiency, and reduce costs, as well as promote standardization of health care.

In embodiments, the identifier chip 822 may be removably affixed to the faceplate 802. In some embodiments, the identifier chip 822 may be removably affixed to the faceplate 802 through a receiving slot 824, wherein the receiving slot 824 is integrated into the exterior surface 806 of the faceplate 802. In an embodiment, the identifier chip 822 may be affixed to the faceplate 802 in any manner. In another embodiment, the identifier chip 822 may be affixed to the faceplate 802 in any manner provided that the machine-readable identifier 826 is visible from the exterior surface 806 of the faceplate 802. Affixing the identifier chip 822 may activate the faceplate module (shown in FIG. 10 as reference numeral 1006) and trigger the faceplate module to communicate with the medical device 804 and with the hospital's network. As utilized herein, the hospital's network is not meant to be limiting, and maybe broadly refer to any and all networks or systems configured to coordinate the storage and retrieval of medical device information and associated data.

In other embodiments, the machine-readable identifier may be an RFID (e.g. a near-field communication identifier tag) or a tag adapted for use in an RTLS that is not visible upon the exterior surface of a faceplate of a medical device. In further embodiments, the machine-readable identifier includes one or more of a barcode, an RFID, or a tag adapted for use in an RTLS, such that a scanning device, an RFID-reading device, or a locating device may be used to identify the medical device.

Figure 10:
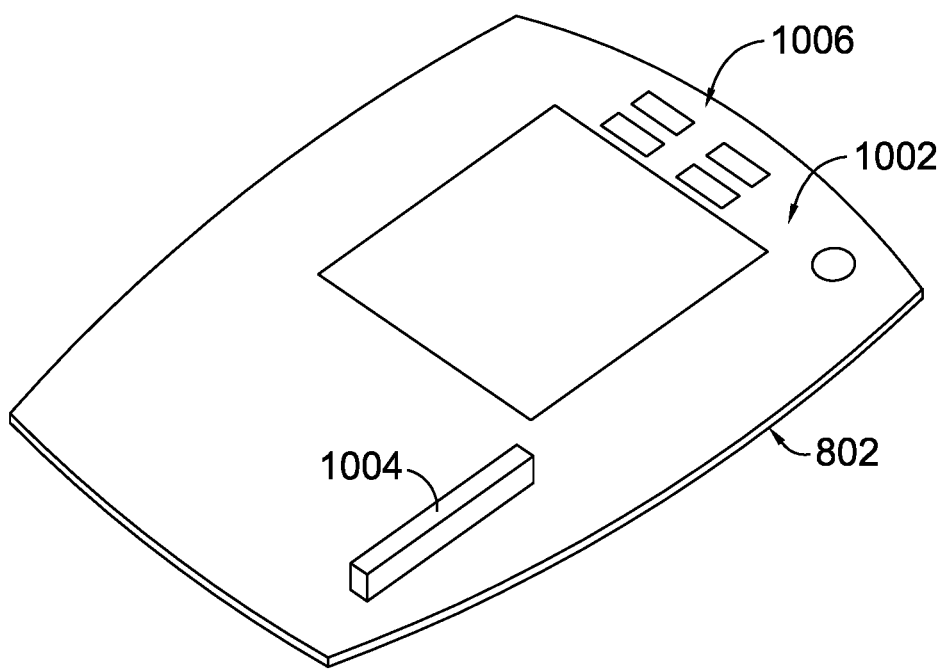
FIG. 10 is a plan view of an interior surface of an exemplary faceplate for a medical device, in accordance with an embodiment of the invention.

In embodiments, the identifier chip 822 may communicate with the faceplate module through a wired connection (not shown) to the faceplate module (shown in FIG. 10 as reference numeral 1006). In other embodiments, the identifier chip 822 may communicate with the faceplate module 1006 through a wireless connection. To communicate with the faceplate module 1006, the identifier chip 822 may utilize RFID, Near-Field Communication (NFC), Wi-Fi, Low-Power Wi-Fi, Bluetooth, Bluetooth Low Energy (BLE), or any other wireless communication system now known or later developed.

In embodiments, the faceplate 802 includes an opening 812 for housing a window 818. The opening 812 is adapted to receive at least a portion of a window 818, in embodiments. The opening 812 may further be adapted to securely retain at least a portion of a window 818 inserted or positioned therein. Generally, the opening 812 may be similar or the same in size and shape as a window 818 adapted for said opening 812. In embodiments, the position and dimensions of the opening 812 and the window 818 correspond to the position and dimensions of a visual communication alert indicator 810 on a surface of the medical device adjacent to the interior surface of the faceplate (shown in FIG. 9 as reference numeral 830).

In further embodiments, the position and dimensions of a first opening 812 correspond to the position and dimensions of a first window (e.g. 818) and a visual communication alert indicator 810, while the position and dimensions of a second opening (e.g., opening 814) correspond to the position and dimensions of a second window (e.g., window 816) further corresponding to the GUI 808 of a medical device 804.

In embodiments, window 818 is adapted to be secured to the faceplate 802 so as to span opening 812 completely or at least partially. In some embodiments, window 818 is adapted to be integrated into opening 812. The window 818 is at least semi-transparent, in embodiments. The window 818 provides visibility of the visual communication alert indicator 810 via the opening 812 to the exterior surface 806 of the faceplate 802. As such, the window 818 may be positioned so that the visual communication alert indicator 810 is visible when the faceplate 802 is viewed from the exterior surface 806.

In embodiments, the visual communication alert indicator 810 is connected to the faceplate module (shown in FIG. 10 as reference numeral 1006). It will be understood by those in the art that the connection between the visual communication alert indicator 810 and the faceplate module can take the form of any suitable connection now known or later developed. As discussed in detail below, the visual communication alert indicator 810 can comprise any device or system that provides visual stimuli to a user. For example, the visual communication alert indicator 810 may comprise a multi-wavelength light emitting diode (LED) wherein the LED emits a predetermined wavelength for a predetermined interval based on a predetermined status condition of the faceplate 802 and/or the medical device 804. For instance, the visual communication alert indicator 810 may: maintain a solid green color to indicate that both the faceplate 802 and the medical device 804 are in proper working order and not in use; flash a green color intermittently to indicate that the faceplate 802 and the medical device 804 are proper working order and the medical device 804 is in use; maintain a solid yellow color to indicate that the faceplate 802 is currently storing a medical device update that has yet to be pushed to and installed on the medical device 804; and/or, flash a red color intermittently to indicate that the faceplate 802 and/or the medical device 804 are not in proper working order. It will be well understood by those skilled in the art that the preceding example is not limiting and in no way indicative of all of the possible uses and/or signaling methods that the visual communication alert indicator 810 is capable of; to that end, the preceding example is provided merely as an illustrative example of one of the many embodiments contemplated by the inventors.

In some embodiments, the medical device system 700 may need refurbishment or replacement of parts, such as the faceplate 802 that fits onto the housing of the medical device 804. The faceplate 802 may include a plurality of objects 820 for user interaction. In embodiments, the faceplate 802 may include one or more of the following objects for controlling, programming, and adjusting configurations and functions of the medical device: a GUI (e.g., 808), I/O components, physical buttons, virtual buttons, switches, dials, knobs, a keyboard, and the like, for example. The plurality of objects 820 may be manipulated by a user, such as a clinician, in order to use the medical device system 700 to provide health care services to a patient. Over time, one or more of the plurality of objects 820 may wear out from use, such that at least one of the objects 820 may be unresponsive when depressed, may necessitate the use of extra force to elicit the desired response (e.g., selection of an option indicated on the GUI 808, increasing an amount to be dispensed by a medical device, setting a flow rate), or may necessitate the use of several depressions to register a single depression that elicits a response. This makes interaction with the medical device system 700 an inconvenience and an annoyance for clinicians. At such a time, any worn-out, malfunctioning, and/or poorly operating objects of the faceplate 802 may be replaced to restore fully functioning interactive objects to the medical device system 700.

Figure 9:
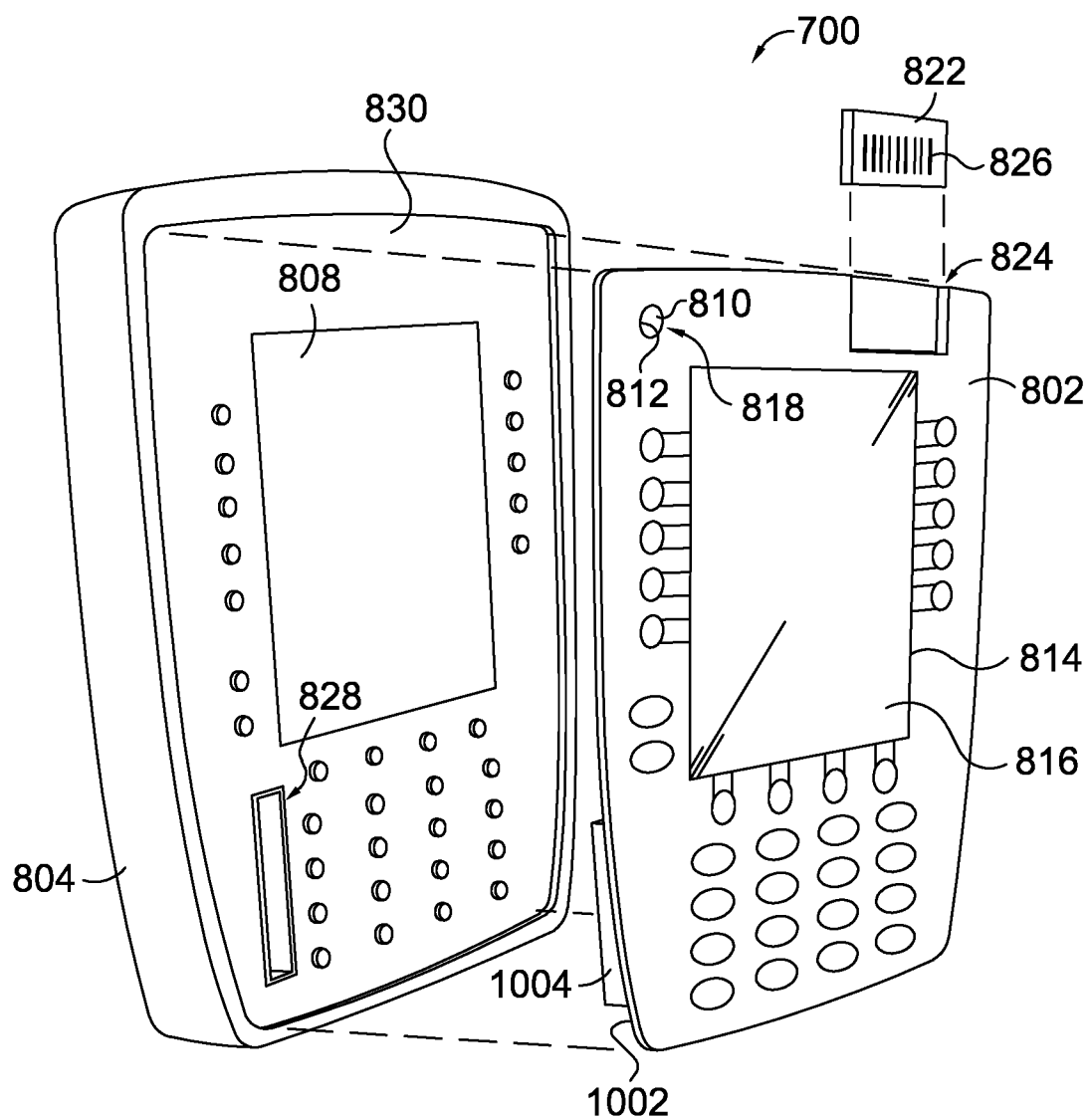
FIG. 9 is an exploded perspective view of the exemplary medical device including a faceplate shown in FIG. 7, in accordance with an embodiment of the invention.

FIG. 9 depicts an exploded view of the exemplary medical device system 700 shown in FIG. 7 including a faceplate 802 and a medical device 804, in accordance with an embodiment of the present invention. As discussed above, in an embodiment of the present invention the identifier chip 822 may be removably affixed to the faceplate 802 through a receiving slot 824, wherein the receiving slot 824 is integrated into the exterior surface of the faceplate 806. However, in other embodiments not depicted, the identifier chip 822 may be affixed to the faceplate 802 in any manner, as is also discussed above. As illustrated in FIG. 9, the second window (e.g., window 816) shown positioned in second opening 814 provides protection to the GUI 808 of a medical device 804. Although not shown in FIG. 9, in embodiments the window 818 shown as positioned in opening 812 provides protection to a visual communication alert indicator 810 positioned on the medical device 804, such that the visual communication alert indicator 810 may be enclosed between the interior surface of the faceplate 802 and the adjacent surface 830 of the housing of the medical device 804.

In embodiments, the faceplate 802 has a communication port (shown in FIG. 10 as reference numeral 1004) positioned on the interior face (shown in FIG. 10 as reference numeral 1002) of the faceplate 802. The communication port 1004 is adapted such that it removably affixes to the receiving port 828 on an adjacent surface 830 of the medical device. Generally, the communication port 1004 may be the inverse in size and shape as the receiving port 828. In embodiments, the position, size, shape, and dimensions of the communication port 1004 correspond to the position and dimensions of the receiving port 828. In such embodiments, the communication port 1004 and the receiving port 828 are such that a connection suitable for the transfer of electronic information and/or signals is created between the medical device 804 and the faceplate module 1006 when the faceplate 802 is removably affixed to the medical device 804. In alternative embodiments not depicted, the communication port 1004 and the receiving port 828 may comprise any wireless communication system now known or developed suitable for transferring electronic information and/or signals between the faceplate module 1006 and the medical device 804. As nonlimiting examples, the communication port 1004 and the receiving port 828 may utilize Near Field Communication (NFC), Wi-Fi, Low-Power Wi-Fi, Bluetooth, Bluetooth Low Energy (BLE), or any other wireless communication system to establish wireless communication.

In either configuration the communication port 1004 and the receiving port 828 could, for example, allow the faceplate module 1006 to: assess the status of the medical device 804; determine if the medical device 804 is in proper working order; determine if the medical device 804 can accept an update from the faceplate module 1006; push an update to the medical device 804; install an update on the medical device 804; verify the integrity of an update on the medical device 804; request medical device data, such as identification data, usage data, maintenance data, and/or diagnostic data; and/or, periodically or continuously monitor the medical device 804. It will be well understood by those skilled in the art that the preceding examples are not limiting and in no way indicative of all of the possible uses of the communication port 1004 and the receiving port 828. To that end, the preceding examples are merely illustrative examples of some of the uses contemplated by the inventors.

Additionally, in embodiments the communication port 1004 and the receiving port 828 are configured such that a connection suitable for the transfer of power is created when the faceplate 802 is removably affixed to the medical device 804. In alternative embodiments, a dedicated wireless power transfer system (not shown), such as a dedicated electromagnetic induction system, may be used to facilitate the transfer of power between the faceplate module 1006 and the medical device 804. In either configuration the communication port 1004 and the receiving port 828 could, for example, allow the faceplate module 1006 to charge the faceplate module's power supply and/or allow the faceplate module 1006 to power the medical device 804.

FIG. 10 illustrates a perspective view of the faceplate 802 of FIG. 9, in accordance with an embodiment of the present invention. As illustrated, the faceplate 802 includes an interior surface 1002. The interior surface 1002 of the faceplate 802 comprises a communication port 1004, a visual communication alert indicator 810, and a faceplate module 1006. In embodiments the faceplate module 1006 comprises at least at least one processor, computer readable memory, a power supply, a wireless receiver, and a wireless transmitter.

In embodiments, the faceplate module 1006 is configured to connect to the hospital's network and communicate the association of the faceplate 802 with the medical device 804. The communication may include additional information as well, depending on the embodiment. For instance, in some embodiments the faceplate module 1006 further comprises a GPS receiver. In such embodiments the faceplate module may communicate the GPS-determined location of the medical device system 700 to the network to facilitate tracking and significantly reduce the burden on hospital personnel in locating lost, damaged, or malfunctioning medical devices.

In embodiments, the faceplate module 1006 further comprises a motion sensor. In such embodiments the faceplate module 1006 may receive a signal from the motion sensor indicating the medical device 804 may be in use. The faceplate module 1006 may interpret such a signal as indication that the medical device 804 is not in a condition suitable to receive a medical device update. For instance, if the faceplate 802 is affixed to a smart IV pump, the motion sensor may detect the small vibrations created by the pump mechanism when the pump mechanism is in use. The faceplate module 1006 may receive the electronic signal from the motion sensor and may determine that the smart pump is currently in use dispensing intravenous fluids and/or medication to a patient. The faceplate module 1006 would delay pushing the smart pump update to the smart pump until the faceplate module 1006 no longer receives the signal from the motion detector indicating active use. In embodiments, the faceplate module 1006 may use signals from the motion sensor in combination with communication with the medical device 804 to verify the status of the medical device 804 and ensure that the medical device 804 is in a condition suitable to receive and install the medical device update.

Additionally, in embodiments the faceplate module 1006 may receive an indication from a hospital network that the there is a pending medical device update for the medical device 804 with which the faceplate 802 is associated. For example, the update may be a drug library, formulary, or other device update. The update may, as such, comprise computer readable associations of drug name, drug concentration, standard dosing rates, counter-indications, and/or any information related to the delivery of IV drugs to a patient. The faceplate module 1006 may also signal that the faceplate module 1006 is ready to receive the medical device update. The faceplate module 1006 may receive and store the medical device update, at least temporarily, in the faceplate module's computer-readable memory. As used herein computer-readable memory refers to any memory system now known or later developed capable of storing computer-readable data, such as RAM, Flash Memory, Solid State Drives (SSD), traditional hard drives (e.g. HDD), and their like. It will be understood by those skilled in the art that the preceding list is merely an illustrative example of types of computer-readable storage consistent with the present invention and not meant as an exhaustive or limiting expression of the computer-readable storage compatible with the present invention.

In embodiments, the faceplate module 1006 may communicate with the identifier chip 822. The communication between the identifier chip 822 and the faceplate module 1006 may include the faceplate module 1006 receiving an activation signal from the identifier chip 822 that activates the faceplate module 1006. Once activated, the faceplate module 1006 may request identification information from the identifier chip 822 and the medical device 804. The faceplate module 1006 may associate the identification information from the identifier chip 822 and the medical device 804 and transmit the identification information and/or the association between the identifier chip 822 and the medical device 804 to the hospital network to coordinate the storage and retrieval of medical device information and associated data.

In alternative embodiments, the faceplate module 1006 may "read" the identifier chip 822 and request identification information from the medical device 804. The faceplate module 1006 may associate the identification information from the identifier chip 822 and the medical device 804 and transmit the identification information and/or the association between the identifier chip 822 and the medical device 804 to the hospital network to coordinate the storage and retrieval of medical device information and associated data.

In embodiments, the faceplate module 1006 may store identification information and/or the association between the identifier chip 822 and the medical device 804. In response to a notification from the hospital's network that there is an available medical device update for a specified medical device, the faceplate module 1006 may determine if the specified medical device is of a type consistent with the medical device 804, the identifier chip 822, and/or the association between the identifier chip 822 and the medical device 804. If the update is consistent, the faceplate module 1006 may receive and store, at least temporarily, the medical device update.

In embodiments, the faceplate module 1006 may be powered by the faceplate module power supply. In embodiments, the faceplate module power supply may be a re-chargeable battery. Those skilled in the art will understand that any rechargeable battery suitable for use in a clinical environment will also be suitable for use in the present invention. For example, Nickel-Cadmium (NiCd, or NiCad), Nickel-Metal Hydride (NiMH, or Ni—MH), Lithium ion (Li-ion), and Lithium Polymer (LiPo, LIP, Li-poly, etc.) are all suitable for use in the present invention; however, this list is merely illustrative and not meant to be limiting.

As discussed above, in embodiments, the faceplate module 1006 may be configured to transfer power from the medical device 804 to directly power the faceplate 802 and the faceplate module 1006. As discussed above, this may be done through the communication port 1004 in some embodiments. In some embodiments, a dedicated wireless power transfer system (not shown) may be used to transfer power from the medical device 804 to the faceplate module 1006, also discussed above. Additionally, in some embodiments, the faceplate module 1006 may be configured to transfer power to the medical device 804 to directly power the medical device 804. As discussed above, this may be done through the communication port 1004 in some embodiments. In some embodiments, a dedicated wireless power transfer system (not shown) may be used to transfer power from the faceplate module 1006 to the medical device 804, also discussed above. The faceplate module 1006 with such a power transfer system may be used in any number of useful ways. For instance, a faceplate module 1006 so configured would not require an independent connection to a wall socket and could instead be powered through the same connection the medical device 804 is using. Further, if the faceplate module 1006 determines that the medical device 804 is not connected to a wall socket and, for example, determines that the medical device's battery backup is below a predetermined threshold, the faceplate module 1006 may communicate an alert to the network indicating the medical device's status and location. Additionally, a faceplate module 1006 so configured could: receive and store a medical device update; determine that the medical device 804 is powered off and not plugged into a wall socket; determine that the medical device's battery backup is below a predetermined threshold; determine that the faceplate module's power supply has enough power to power the medical device 804; transfer power to the medical device 804; power on the medical device 804; push the medical device update to the medical device 804; trigger the installation of the medical device update; verify the medical device update; power off the medical device 804; and transmit a verification signal to the network.

In embodiments, the faceplate module 1006 may provide status notifications to a user through the visual communication alert indicator 810. In embodiments, the faceplate module 1006 may determine what status notification to signal based on the status of the faceplate module, the status of the faceplate 802, and/or the status of the medical device 804. For example, the faceplate module 1006 may use the visual communication alert indicator 810 to produce: a first visual stimulus to indicate the initial association with the identifier chip 822, for example a rapidly flashing green color; a second visual stimulus to indicate the establishment of a successful connection, through the communication port 1004, with the medical device 804, for example two green flashes and then a brief pause; a third visual stimulus to indicate successful connection to the network, for example three green flashes, and a brief pause; a fourth visual stimulus to indicate that all systems are operating appropriately, for example a solid green color; a fifth visual stimulus to indicate a malfunction, error, or fault in one or more components of the faceplate 802, the faceplate module 1006, and/or the medical device 804 requiring service, for example a solid red color; a sixth visual stimulus to indicate a medical device update is being acquired from the network, for example a flashing yellow color; a seventh visual stimulus to indicate a medical device update is stored in the faceplate module 1006 and the faceplate module 1006 is waiting for the medical device 804 to be in condition to install the update, for example alternating green and yellow colors; and, an eighth visual stimulus to indicate the faceplate module 1006 is currently pushing, installing, or verifying a medical device update on the medical device 804, for example a continuous yellow color. As those skilled in the art will understand, the preceding example is merely illustrative and the faceplate module 1006 may display additional, alternative, or fewer visual communication signals through the visual communication alert indicator 810 and remain consistent with the presently disclosed invention. Additionally, those skilled in the art will understand that the faceplate module 1006 may use customizable visual stimuli in combination with the visual communication alert indicator 810 as determined by the user or hospital policy.

In an alternative embodiment the visual communication alert indicator 810 may consist of a LCD display screen. In such an embodiment, the faceplate module may be configured to use the visual communication alert indicator 810 to display other similar visual stimuli to notify users of similar status alerts. In an alternative embodiment, the visual communication alert indicator 810 may consist of any device or system capable of communicating with a user. In such embodiments the faceplate module 1006 is configured to utilize the visual communication alert indicator 810 in a manner similar to those discussed in detail directly above.

As discussed in detail above, in some embodiments, the communication port 1004 is configured such that the communication port 1004 may be removably affixed to the receiving port 804. Further, in some embodiments the position, size, shape, and dimensions of the communication port 1004 correspond to the position and dimensions of the receiving port 828. In alternative embodiments, the communication port 1004 and the receiving port 828 are configured such that wireless communication is possible between the faceplate module 1006 (via the communication port 1004) and the medical device 804 (via the receiving port 828).

As those skilled in the art will understand, the faceplate module 1006 may comprise additional, alternative, or fewer components depending on the medical device 804 and the desires of the user. Additionally, the faceplate module 1006 may comprise multiple sub-components, components not specifically identified herein, or any number of sub-components in a unified or modular system without deviating from the invention described herein. For example, the wireless receiver and wireless transmitter may be contained in a single component, such as a WIFI card. Further, in embodiments the faceplate module 1006 may incorporate the visual communication alert indicator 810 and/or the communication port 1004 into a unified or modular system without deviating from the invention described herein.

Figure 11:
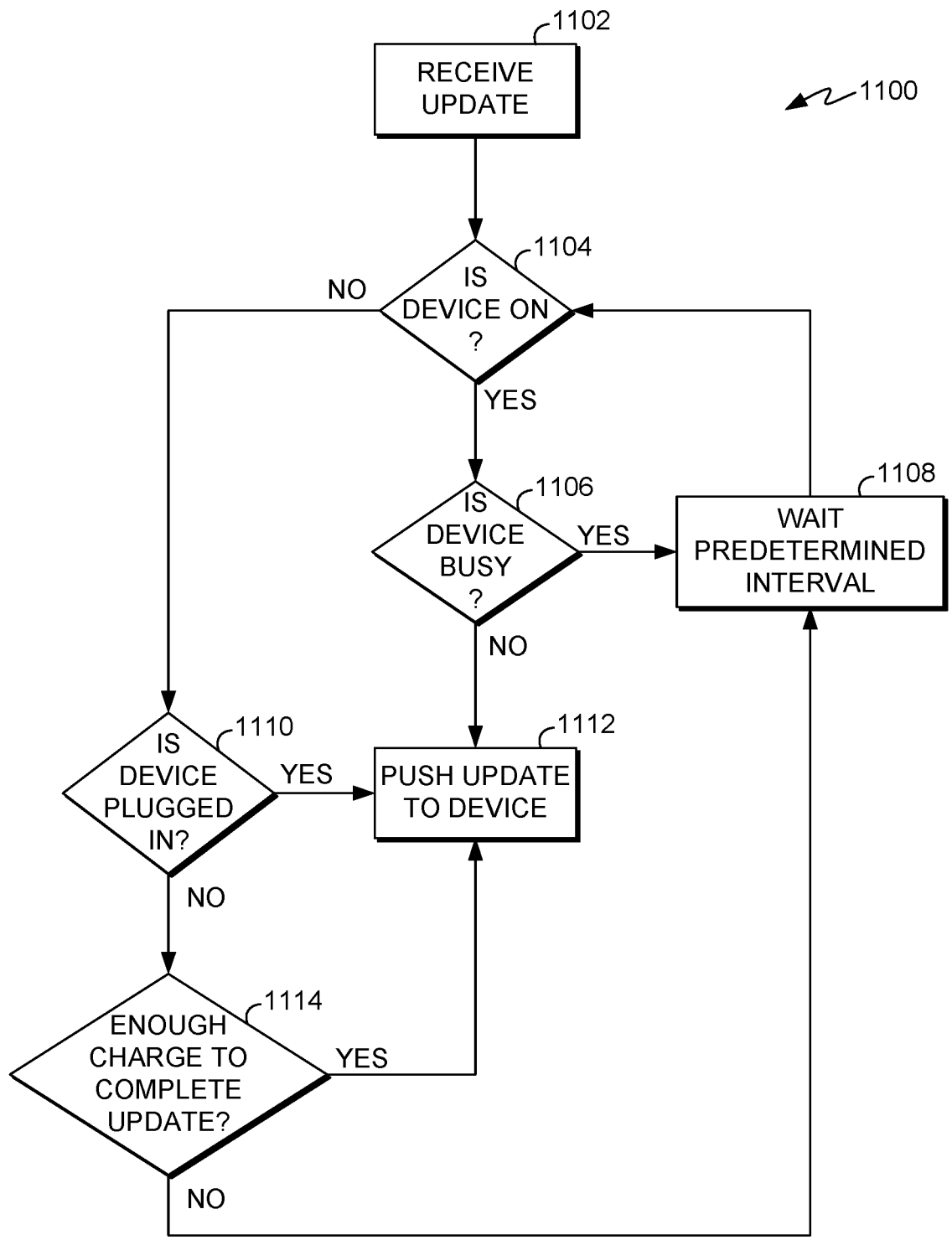
FIG. 11 is an illustrative flow diagram of an exemplary method for utilizing a faceplate shown in FIG. 7, in accordance with an embodiment of the invention.

FIG. 11 illustrates a flow chart of an exemplary method 1100 for utilizing the present invention. At block 1102, the method 1100 includes receiving a medical device update, such as a smart pump formulary update, for example. Next, the faceplate determines if the medical device with which it is associated is powered on, as shown at block 1104. If the faceplate determines that the medical device is powered on, the faceplate then determines if the medical device is busy, as shown at block 1106. If the faceplate determines that the medical device is not busy—i.e., that it is not engaged in a task which would disrupt or be disrupted by the installation of the medical device update—the faceplate will push the update to the medical device and install the update, as shown at block 1112. Returning to block 1106, if the faceplate determines that the medical device is busy, as defined above, the faceplate will wait a predetermined interval, as shown at block 1108. After waiting the predetermined interval the faceplate will return to block 1104 and determine if the medical device is powered on.

If at block 1104 the faceplate determines the medical device is not powered on, the faceplate determines if the medical device is plugged in, as shown at block 1110. If the faceplate determines that the medical device is plugged in, the faceplate will power on the medical device and the faceplate will push the update to the medical device and install the update, as shown at block 1112. Returning to block 1110, if the faceplate determines that the medical device is not plugged in, the faceplate will determine if the faceplate or the medical device has enough battery power to complete the update, as shown at block 1114. If the faceplate determines that the medical device or the faceplate itself have enough battery power to complete the update, the faceplate will power on the medical device, push the update to the medical device, and install the update, as shown at block 1112. However, if the faceplate determines the medical device or the faceplate itself do not have enough battery power to complete the update, the faceplate will wait a predetermined interval, as shown at block 1108. After waiting the predetermined interval, the faceplate will return to block 1104 and determine if the medical device is powered on. It will be understood by those in the art that the method 1100 may be practiced utilizing exemplary device 700, for example, and that implementing the present invention may incorporate additional, fewer, or alternative steps to those shown in exemplary method 1100. It will also be understood that the steps shown in exemplary method 1100 may be performed in any number of different orders consistent with the present invention.

Figure 12:
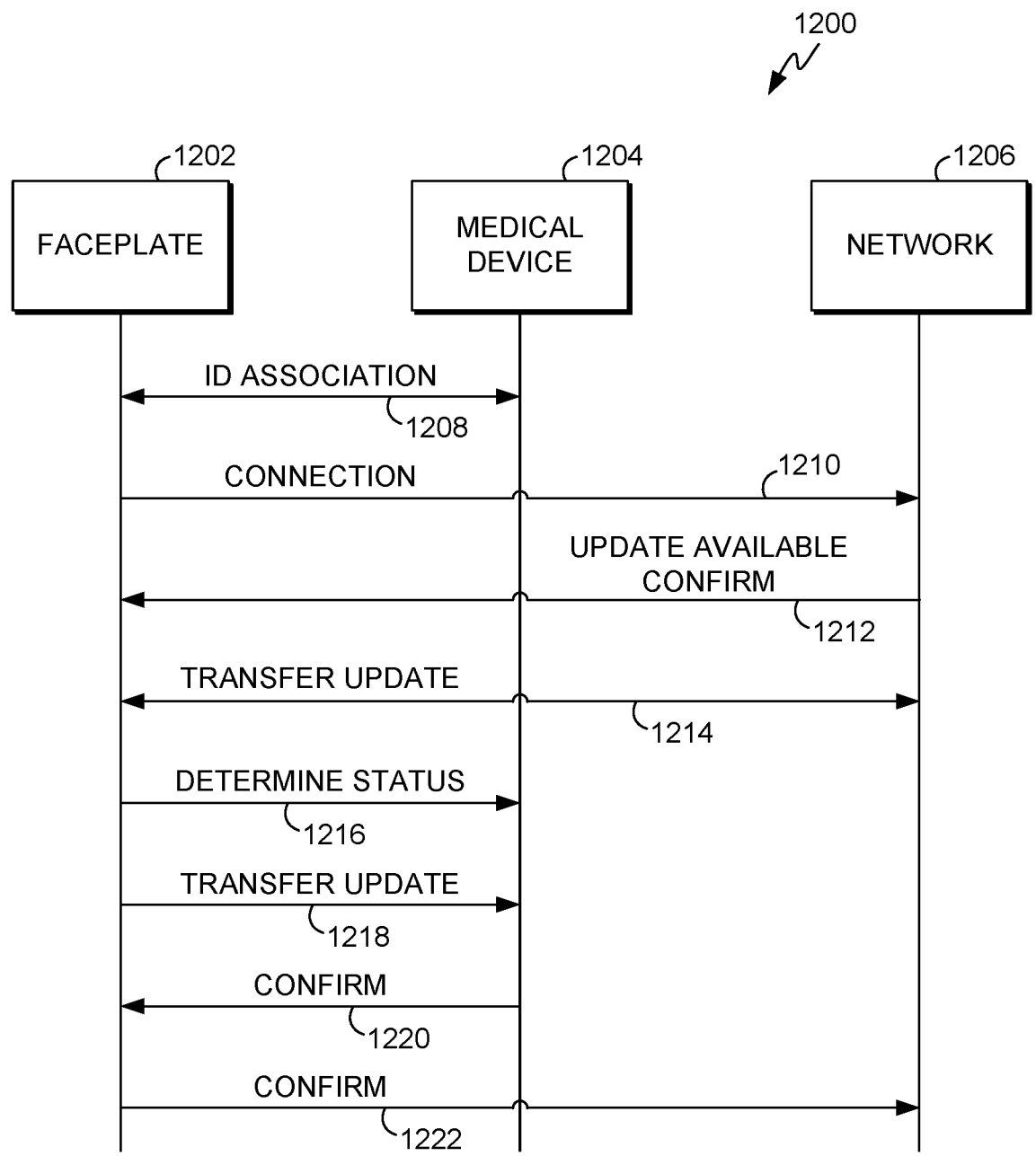
FIG. 12 is an illustrative flow diagram of another exemplary method for utilizing a faceplate shown in FIG. 7, in accordance with an embodiment of the invention.

FIG. 12 illustrates a flow chart of an exemplary method 1200 for: associating the faceplate 1202 with the medical device 1204; connecting the faceplate to the hospital's network 1206; and, receiving an update from the hospital's network, installing the update on the medical device and ultimately confirming the installation of the update with the hospital's network. As shown at block 1208, the faceplate 1202 requests identification information from the medical device 1204 and associates that information with the faceplate 1202. In some embodiments, the faceplate 1202 associates the medical device 1204 with the identifier chip (not shown). Next, the faceplate 1202 connects with the hospital network 1206 and provides identification information to the network, as shown at block 1210. Next, the hospital's network 1206 indicates to the faceplate 1202 that an update is available for the medical device 1204, as shown at block 1212. Next, as shown at block 1214, the network 1206 transfers the update to the faceplate 1202 and the faceplate 1202 verifies the update with the network 1206. Next, the faceplate 1202 determines the status of the medical device 1204, as shown at block 1216. Next, the faceplate 1202 transfers the update to the medical device 1204, as shown at block 1218. Next, the medical device 1204 confirms the update with the faceplate 1202, as shown at block 1220. Finally, the faceplate confirms the transfer of the update to the medical device 1204 with the network 1206, as shown at block 1222.

It will be understood by those in the art that implementing the present invention may incorporate additional, fewer, or alternative steps to those shown in exemplary method 1200. It will also be understood that the steps shown in exemplary method 1200 may be performed in any number of different orders consistent with the present invention. Additionally, it will be understood by those in the art that any given step in exemplary method 1200 may include additional steps not explicitly recited herein but contemplated by the inventors. For example, blocks 1206 and 1218 may include all of, or portions of, exemplary method 1100.

Many different arrangements of the various components depicted, as well as components not shown, are possible without departing from the scope of the claims below. Embodiments of our technology have been described with the intent to be illustrative rather than restrictive. Alternative embodiments will become apparent to readers of this disclosure after and because of reading it. Alternative means of implementing the aforementioned can be completed without departing from the scope of the claims below. Certain features and subcombinations are of utility and may be employed without reference to other features and subcombinations and are contemplated within the scope of the claims.

The invention claimed is:

1. A medical device, the device comprising:
a housing and a first communication port;
the housing configured to removably affix a faceplate, wherein the faceplate comprises at least one processor, computer readable memory, a power supply, a wireless receiver, a wireless transmitter, and a second communication port, wherein the first communication port is adapted to communicate with the second communication port.

2. The device of claim 1, wherein the first communication port wirelessly communicates with the second communication port.

3. The device of claim 1, wherein the medical device receives power from the faceplate.

4. The device of claim 3, wherein the medical device wirelessly receives power from the faceplate.

5. The device of claim 1, wherein the medical device is an intravenous pump.

6. The device of claim 1, wherein the faceplate further comprises a visual communication alert indicator, and wherein the visual communication alert indicator indicates a status of the faceplate or the medical device.

7. A medical device comprising:
a housing and a communication port;
the housing configured to removably affix a faceplate, wherein the faceplate communicatively couples to the medical device through the communication port of the medical device, and wherein an exterior surface of the faceplate further comprises an identifier chip adapted to be removably affixed to the exterior surface of the faceplate.

8. The device of claim 7, wherein the communication port is wirelessly couples with the faceplate.

9. The device of claim 7, wherein the medical device receives power from the faceplate.

10. The device of claim 9, wherein the medical device wirelessly receives power from the faceplate.

11. The device of claim 7, wherein the faceplate is communicates an update to the medical device via the communication port.

12. The device of claim 7, wherein the medical device is an intravenous pump.

13. The device of claim 7, wherein the faceplate further comprises a visual communication alert indicator, and wherein the visual communication alert indicator indicates a status of the faceplate or the medical device.

14. A wireless communication device integrated with a faceplate, the device comprising:
a faceplate removably affixable to a medical device's housing;
the faceplate comprising at least a wireless communication device and a communication port, the communication port adapted to communicate with the medical device, and wherein an exterior surface of the faceplate further comprises an identifier chip adapted to be removably affixed to the exterior surface of the faceplate.

15. The device of claim 14, wherein the communication port wirelessly communicates with the medical device.

16. The device of claim 14, wherein the communication port removably connects to a surface of the medical device adjacent to an interior surface of the faceplate.

17. The device of claim 14, wherein the faceplate further comprises a visual communication alert indicator, and wherein the visual communication alert indicator indicates a status of the faceplate or the medical device.

18. The device of claim 14, wherein the identifier chip is adapted to communicate data associated with the identifier chip to the faceplate.

19. The device of claim 14, wherein the faceplate provides power to the medical device.

* * * * *

UNITED STATES PATENT AND TRADEMARK OFFICE
CERTIFICATE OF CORRECTION

PATENT NO. : 10,940,262 B2
APPLICATION NO. : 15/703526
DATED : March 9, 2021
INVENTOR(S) : Alan Mark Portnoy It is certified that error appears in the above-identified patent and that said Letters Patent is hereby corrected as shown below:

On the Title Page

Column 2, Item (57) Abstract, Line 8: After "cues" please insert --to--.

In the Specification

Column 3, Line 66: Please remove "end title" and replace with --end-tidal--.

Column 9, Line 49: Please remove "and or" and replace with --and/or--.

Column 9, Line 59: Please remove "and or" and replace with --and/or--.

Column 9, Line 60: Please remove "device" and replace with --device.--.

Column 20, Line 24: Please remove "is wirelessly" and replace with --wirelessly--.

Column 20, Line 29: After "faceplate" please remove --is--.

Signed and Sealed this
Twenty-first Day of February, 2023

Katherine Kelly Vidal
*Director of the United States Patent and Trademark Office*